(12) United States Patent
Thibault Pelletier et al.

(10) Patent No.: US 11,751,835 B2
(45) Date of Patent: Sep. 12, 2023

(54) RADIOGRAPHIC IMAGING APPARATUS

(71) Applicant: Shimadzu Corporation, Kyoto (JP)

(72) Inventors: David Thibault Pelletier, Laval (CA); Shota Sato, Kyoto (JP); Shohei Okubo, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 528 days.

(21) Appl. No.: 16/635,700

(22) PCT Filed: Apr. 19, 2018

(86) PCT No.: PCT/JP2018/016136
§ 371 (c)(1),
(2) Date: Jan. 31, 2020

(87) PCT Pub. No.: WO2019/053935
PCT Pub. Date: Mar. 21, 2019

(65) Prior Publication Data
US 2020/0330063 A1 Oct. 22, 2020

(30) Foreign Application Priority Data

Sep. 14, 2017 (JP) .................................. 2017-177004

(51) Int. Cl.
*A61B 6/00* (2006.01)
*A61B 6/06* (2006.01)
(Continued)

(52) U.S. Cl.
CPC .............. *A61B 6/5235* (2013.01); *A61B 6/06* (2013.01); *A61B 6/481* (2013.01); *A61B 6/504* (2013.01);
(Continued)

(58) Field of Classification Search
None
See application file for complete search history.

(56) References Cited

U.S. PATENT DOCUMENTS

| | | | | |
|---|---|---|---|---|
| 4,542,459 A | * | 9/1985 | Riederer | ................ A61B 6/504 378/98.12 |
| 5,892,840 A | * | 4/1999 | Jang | ........................ G06T 7/194 378/162 |

(Continued)

FOREIGN PATENT DOCUMENTS

| JP | 2003265408 A | 9/2003 |
|---|---|---|
| JP | 2006087631 A | 4/2006 |
| JP | 2007-215930 A | 8/2007 |

OTHER PUBLICATIONS

Written Opinion by the International Search Authority for PCT application PCT/JP2018/016136, dated Jun. 26, 2018, submitted with a machine translation.

(Continued)

*Primary Examiner* — Michelle M Entezari
(74) *Attorney, Agent, or Firm* — Muir Patent Law, PLLC (57) ABSTRACT

A radiographic imaging apparatus (100) is configured to generate movement maps (30) of pixels (21) belonging to a first image (11) based on the first image (11) and a second image (12) captured at different times, to move a pixel (21) of the first image (11) based on a smoothed movement map (30*a*) in which high-frequency components of the movement maps (30) have been suppressed in a spatial direction and generate a deformed image (11*a*), and to combine the deformed image (11*a*) and the second image (12).

11 Claims, 6 Drawing Sheets

(51) Int. Cl.
   *G06T 5/00* (2006.01)
   *G06T 5/50* (2006.01)
   *G06T 7/00* (2017.01)
   *G06T 7/20* (2017.01)

(52) U.S. Cl.
   CPC .......... *A61B 6/5211* (2013.01); *A61B 6/5217* (2013.01); *G06T 5/002* (2013.01); *G06T 5/50* (2013.01); *G06T 7/0012* (2013.01); *G06T 7/20* (2013.01); *G06T 2207/10116* (2013.01); *G06T 2207/20212* (2013.01); *G06T 2207/30101* (2013.01)

(56) References Cited

U.S. PATENT DOCUMENTS

| | | | | |
|---|---|---|---|---|
| 6,004,270 | A * | 12/1999 | Urbano | G06T 7/38 600/443 |
| 6,192,265 | B1 * | 2/2001 | Carlsen | G06T 11/005 324/309 |
| 6,532,380 | B1 * | 3/2003 | Close | A61B 6/481 600/407 |
| 7,545,967 | B1 * | 6/2009 | Prince | G06T 5/50 382/280 |
| 2003/0048935 | A1 * | 3/2003 | Keren | A61B 6/504 382/130 |
| 2006/0002630 | A1 * | 1/2006 | Fu | G06V 10/24 382/294 |
| 2007/0195931 | A1 | 8/2007 | Ohishi | |
| 2007/0195932 | A1 * | 8/2007 | Nakaura | G06T 7/20 378/98.12 |
| 2008/0012563 | A1 * | 1/2008 | Weiss | G01R 33/56 324/307 |
| 2008/0037845 | A1 * | 2/2008 | Deuerling-Zheng | G06T 7/238 382/130 |
| 2008/0037869 | A1 * | 2/2008 | Zhou | H04N 5/145 382/173 |
| 2008/0204592 | A1 * | 8/2008 | Jia | G06T 3/4007 375/E7.123 |
| 2009/0005670 | A1 * | 1/2009 | Ichinose | A61B 5/055 600/410 |
| 2010/0067660 | A1 * | 3/2010 | Maurer, Jr. | A61B 6/486 378/95 |
| 2011/0103480 | A1 * | 5/2011 | Dane | H04N 19/527 375/E7.123 |
| 2011/0128379 | A1 * | 6/2011 | Lee | G06T 7/269 348/E7.085 |
| 2011/0142313 | A1 * | 6/2011 | Pack | G06T 7/246 378/4 |
| 2011/0158550 | A1 * | 6/2011 | Noda | H04N 5/3658 382/265 |
| 2011/0213244 | A1 * | 9/2011 | Frinking | A61B 5/055 600/431 |
| 2012/0027282 | A1 * | 2/2012 | Yoshikawa | A61B 8/13 382/131 |
| 2013/0278596 | A1 * | 10/2013 | Wu | G06T 15/00 345/419 |
| 2014/0205066 | A1 * | 7/2014 | Kitagawa | A61B 6/542 378/62 |
| 2014/0307935 | A1 * | 10/2014 | Ishii | A61B 6/5288 382/131 |
| 2015/0010221 | A1 * | 1/2015 | Abe | G06T 5/004 382/130 |
| 2016/0015348 | A1 * | 1/2016 | Ohishi | A61B 6/504 600/431 |
| 2016/0371862 | A1 * | 12/2016 | Silver | A61B 6/504 |
| 2017/0000428 | A1 * | 1/2017 | Goto | A61B 6/54 |
| 2017/0055930 | A1 * | 3/2017 | Hagiwara | G06T 5/20 |

OTHER PUBLICATIONS

Notice of Reasons for Refusal dated Jul. 14, 2020 for corresponding Japanese Patent Application No. 2019-541632, submitted with a machine translation.

Office Action issued by the China Intellectual Property Administration in Chinese Patent Application No. 201880052689.9, dated Jan. 3, 2023, submitted with a machine translation.

* cited by examiner

FIG.4   FLOW OF DSA IMAGE GENERATION USING MOVEMENT VECTORS

*FIG.5*  EXTRACTION OF REGION IN WHICH PIXELS ARE NOT MOVED

*FIG.6*

PIXEL VALUE COMPARISON        IDENTIFY MINIMUM PIXEL VALUE DIFFERENCE PIXEL

FIG.7    GENERATION OF MOVEMENT VECTOR

FIG.8    ADJUSTMENT OF MOVEMENT VECTOR
BASED ON PIXEL VALUE DIFFERENCE

FIG.9

GENERATION OF SMOOTHED MOVEMENT VECTOR

FIG.10

ONE-DIMENSIONALLY ILLUSTRATED MOVEMENT VECTOR

FIG.11

RADIOGRAPHIC IMAGING APPARATUS

TECHNICAL FIELD

The present invention relates to a radiographic imaging apparatus.

BACKGROUND ART

Conventionally, a radiographic imaging apparatus configured to generate first and second images obtained by imaging the same subject at different times and generate a composite image in which a deformed image obtained by moving pixels of the first image and the second image are combined is known. Such a radiographic imaging apparatus is disclosed in Japanese Patent Laid-Open No. 2007-215930, for example.

Japanese Patent Laid-Open No. 2007-215930 discloses a radiographic imaging apparatus including an imager configured to capture a mask image (first image) before contrast medium injection and a contrast image (second image) after contrast medium injection by imaging a subject before and after contrast medium injection. The radiographic imaging apparatus disclosed in Japanese Patent Laid-Open No. 2007-215930 is configured to perform pixel shifting (generate a deformed image) such that one of the mask image and the contrast image is uniformly moved in parallel over an entire arbitrary region in accordance with a pixel shift amount indicating a positional deviation between the mask image and the contrast image in the arbitrary region. The radiographic imaging apparatus disclosed in Japanese Patent Laid-Open No. 2007-215930 is also configured to perform subtraction processing (generate a composite image) between the mask image and the contrast image, one of which has been pixel-shifted.

PRIOR ART

Patent Document

Patent Document 1: Japanese Patent Laid-Open No. 2007-215930

SUMMARY OF THE INVENTION

Problems to be Solved by the Invention

In a radiographic imaging apparatus as disclosed in Japanese Patent Laid-Open No. 2007-215930, as described above, a deformed image is generated in an entire arbitrary region such that artifacts caused by movement of a subject and generated when a composite image is generated between two images captured at different times are reduced. The subject may twist and locally move as well as uniformly move in parallel as a whole.

However, in the radiographic imaging apparatus as disclosed in Japanese Patent Laid-Open No. 2007-215930, one of the first image and the second image is uniformly moved in parallel in the entire arbitrary region such that the deformed image is generated. Therefore, in the radiographic imaging apparatus as disclosed in Japanese Patent Laid-Open No. 2007-215930, it is conceivably difficult to generate the deformed image appropriately with respect to a nonlinear motion (a motion in which linear image processing is impossible over the entire region) of the subject such as a twisting motion and a local motion in which the entire region does not uniformly move in parallel. Thus, in the radiographic imaging apparatus as disclosed in Japanese Patent Laid-Open No. 2007-215930, it is conceivably difficult to appropriately combine the first image and the second image (generate an appropriate composite image) when the subject nonlinearly moves.

The present invention is intended to solve the above problem. The present invention aims to provide a radiographic imaging apparatus capable of appropriately combining two images captured at different times in consideration of not only a linear motion but also a nonlinear motion of a subject between the two images.

Means for Solving the Problems

In order to attain the aforementioned object, a radiographic imaging apparatus according to an aspect of the present invention includes an imager configured to irradiate a subject with radiation and detect the radiation transmitted through the subject to image the subject, an image generator configured to generate a first image and a second image obtained by imaging a same subject at different times, a movement map generator configured to generate movement maps representing moving directions and movement amounts of at least some of pixels belonging to the first image based on the first image and the second image, a smoothed movement map generator configured to generate a smoothed movement map by suppressing high-frequency components of the movement maps in a spatial direction, a pixel movement processor configured to move a pixel of the first image based on the smoothed movement map and generate a deformed image, and a composite image processor configured to generate a composite image in which the deformed image and the second image are combined. The "movement map" is a concept that means a vector representing the moving direction and the movement amount of a pixel. In addition, the "high-frequency component of the movement map in the spatial direction" refers to a portion that is far from the average value due to an error or the like. That is, the expression "suppressing the high-frequency component of the movement map in the spatial direction" refers to suppressing large variations in the moving direction and the movement amount represented by the movement map by reducing (smoothing) generation of the movement map that is far from the average value.

As described above, the radiographic imaging apparatus according to this aspect of the present invention is configured to generate the movement maps of the pixels belonging to the first image based on the first image and the second image captured at the different times, and move the pixels of the first image based on the movement maps and generate the deformed image. Accordingly, the movement map can be generated for each pixel belonging to the first image, and the deformed image can be generated, and thus unlike the case in which the entire region is uniformly moved in parallel and the deformed image is generated, the deformed image in which only a partial region in the first image has been deformed can be generated. Furthermore, as described above, the deformed image is generated based on the smoothed movement map in which the high-frequency components of the movement maps in the spatial direction have been suppressed. Thus, even when an error occurs in the movement map due to generation of the movement map for each pixel, the influence of the error can be reduced by suppressing the high-frequency components in the spatial direction. Consequently, it is possible to appropriately combine the two images captured at the different times in consideration of not only a linear motion but also a nonlinear motion of the subject between the two images.

In the aforementioned radiographic imaging apparatus according to this aspect, the movement map generator is preferably configured to generate the movement maps representing the moving directions and the movement amounts of the pixels of the first image based on pixel value differences between a pixel value of a pixel of the second image and pixel values of the pixel of the first image corresponding to that pixel and pixels belonging to a predetermined surrounding region of the first image. The pixel value is a quantitative value that varies depending on the position of the subject, and thus the pixel value serves as an index of a specific position of the subject in the first image and the second image. Therefore, the pixel value differences between the pixel value of the pixel of the second image and the pixel values of the pixel of the first image corresponding to that pixel and the pixels belonging to the predetermined surrounding region of the first image quantitatively indicate whether or not the predetermined pixel of the second image and the pixels of the first image for which the pixel value differences are obtained correspond to the specific position of the subject. Thus, based on the first image and the second image, the movement map representing the moving direction and the movement amount of each pixel belonging to the first image can be easily generated.

In this case, the movement map generator is preferably configured to generate a movement map representing a moving direction and a movement amount of the pixel of the first image based on the pixel value of the pixel of the second image and a pixel value of a minimum pixel value difference pixel, which is the pixel of the first image having a smallest pixel value difference with respect to the pixel of the second image. Accordingly, the minimum pixel value difference pixel of the first image has the highest probability of being a pixel used as a reference for the second image among that pixel of the first image and the pixels belonging to the predetermined surrounding region of the first image, and thus the movement map can be accurately generated by using the minimum pixel value difference pixel.

In the aforementioned radiographic imaging apparatus according to this aspect, the pixel movement processor is preferably configured to set a movement amount of the pixel of the first image to 0 when a pixel value difference between a pixel value of a pixel of the second image and a pixel value of the pixel of the first image corresponding to that pixel is equal to or less than a first threshold. Accordingly, it is possible to significantly reduce or prevent movement of a pixel of the first image that does not need to be moved due to almost no movement of the pixel of the second image and the pixel of the first image 11 corresponding to that pixel.

The aforementioned radiographic imaging apparatus according to this aspect preferably further includes a collimator configured to narrow down an irradiation region of the radiation to the subject, and a non-irradiation region extractor configured to extract a non-irradiation region of the radiation generated by operation of the collimator in the first image, and the pixel movement processor is preferably configured to set the movement amounts of the pixels of the first image in the non-irradiation region extracted by the non-irradiation region extractor to 0. Accordingly, it is possible to significantly reduce or prevent movement of the pixels in the non-irradiation region of the first image, which are not irradiated with radiation and do not need to be moved can be significantly reduced or prevented. Consequently, it is possible to effectively reduce the control burden on the pixel movement processor when the non-irradiation region is large.

In this case, the non-irradiation region extractor is preferably configured to determine a region of the first image outside boundary pixels as the non-irradiation region, defining pixels adjacent to an outside in a vicinity of top, bottom, left, and right edges of the first image, each of which has a pixel value equal to or greater than a predetermined second threshold, as the boundary pixels. Accordingly, when the pixel value difference between the adjacent pixels in the vicinity of the top, bottom, left, and right edges of the image is equal to or greater than the predetermined value (second threshold), a region in which the adjacent pixels are located is likely to be a boundary between the irradiation region with a high pixel value and the non-irradiation region with a pixel value close to 0 (zero), and thus the pixels in the non-irradiation region of the first image can be easily determined.

The aforementioned radiographic imaging apparatus according to this aspect preferably further includes a direct-ray region extractor configured to extract a direct-ray region in the first image, and the pixel movement processor is preferably configured to set the movement amounts of the pixels in the direct-ray region of the first image extracted by the direct-ray region extractor to 0. Accordingly, it is possible to significantly reduce or prevent movement of the pixels in the direct-ray region, which is a region in the first image in which the subject is not present, that do not need to be moved. Consequently, it is possible to effectively reduce the control burden on the pixel movement processor when the direct-ray region is large.

In this case, the direct-ray region extractor is preferably configured to determine a region of the first image in which pixel values of the pixels that constitute the first image are equal to or greater than a predetermined third threshold as the direct-ray region. Accordingly, the region of the first image in which the pixel values are equal to or greater than the predetermined value (third threshold) is likely to be the direct-ray region in which radiation is directly detected without passing through the subject, and thus the pixels in the direct-ray region of the first image can be easily determined.

In the aforementioned radiographic imaging apparatus according to this aspect, the first image is preferably a non-contrast image that is a radiation image obtained by imaging the subject in a state in which no contrast medium is administered to blood vessels of the subject, and the second image is preferably a contrast image that is the radiation image obtained by imaging the subject in a state in which the contrast medium is administered to the blood vessels of the subject. Accordingly, the contrast image and the non-contrast image captured at the different times can be combined in consideration of not only the linear motion but also the nonlinear motion of the subject between the contrast image and the non-contrast image.

In this case, the radiographic imaging apparatus preferably further includes a blood vessel image pixel extractor configured to extract a pixel that constitutes a blood vessel image in the contrast image, and the pixel movement processor is preferably configured to set a movement amount of a pixel of the non-contrast image corresponding to the pixel that constitutes the blood vessel image to 0. Accordingly, it is possible to significantly reduce or prevent blurriness of the blood vessel image in the composite image in which the contrast image and the non-contrast image are combined due to movement of the pixel of the non-contrast image corresponding to the pixel that constitutes the blood vessel image.

In the aforementioned configuration including the blood vessel image pixel extractor, the blood vessel image pixel extractor is preferably configured to determine a pixel that constitutes the contrast image as the pixel that constitutes the blood vessel image when a pixel value difference between a pixel value of the pixel that constitutes the contrast image and a pixel value of that pixel of the non-contrast image is equal to or greater than a predetermined fourth threshold. Accordingly, when the pixel value difference between the pixel value of the pixel that constitutes the contrast image and the pixel value of the pixel of the non-contrast image corresponding to that pixel is equal to or greater than the predetermined value (fourth threshold), that pixel of the contrast image is likely to be the pixel that constitutes the blood vessel image, and thus the pixel of the blood vessel image in the contrast image can be easily determined.

In the aforementioned configuration in which when the pixel value difference is equal to or greater than the predetermined fourth threshold, the pixel that constitutes the contrast image is determined as the pixel that constitutes the blood vessel image, the pixel movement processor is preferably configured to gradually increase the movement amount of the pixel of the non-contrast image as the pixel value difference between the pixel value of the pixel that constitutes the contrast image and the pixel value of that pixel of the non-contrast image decreases when that pixel value difference is smaller than the predetermined fourth threshold. Because pixels that constitute the blood vessel image are shaded, there is a possibility that the pixel of the contrast image is the pixel that constitutes the blood vessel image even when the pixel value difference between the pixel value of the pixel that constitutes the contrast image and the pixel value of the pixel of the non-contrast image corresponding to that pixel is smaller than the predetermined value (fourth threshold). Furthermore, as the pixel value difference between the pixel value of the pixel that constitutes the contrast image and the pixel value of the pixel of the non-contrast image corresponding to that pixel is closer to the predetermined value (fourth threshold), that pixel of the contrast image is more likely to be the pixel that constitutes the blood vessel image. Therefore, with the aforementioned configuration, in accordance with the possibility that the pixel of the contrast image is not the pixel that constitutes the blood vessel image, the movement amount of the pixel of the non-contrast image corresponding to that pixel can be adjusted.

In the aforementioned configuration including the blood vessel image pixel extractor, the pixel movement processor is preferably configured not to set, to 0, a movement amount of a pixel having a pixel value equal to or less than a predetermined fifth threshold among pixels of the non-contrast image corresponding to pixels of the contrast image determined as pixels that constitute the blood vessel image by the blood vessel image pixel extractor. When in the non-contrast image that does not contain the pixel that constitutes the blood vessel image, the pixel value is equal to or less than the predetermined value (fifth threshold), the pixel is considered as a pixel corresponding to a portion of the subject other than the blood vessel image. Therefore, with the aforementioned configuration, it is possible to significantly reduce or prevent generation of the deformed image without movement of the pixel of the non-contrast image corresponding to the pixel unlikely to be the pixel that constitutes the blood vessel image among the pixels that constitute the contrast image and have been determined as the pixels that constitute the blood vessel image.

EFFECT OF THE INVENTION

According to the present invention, as described above, it is possible to provide a radiographic imaging apparatus capable of appropriately combining the two images captured at the different times in consideration of not only the linear motion but also the nonlinear motion of the subject between the two images.

MODES FOR CARRYING OUT THE INVENTION

An embodiment embodying the present invention is hereinafter described on the basis of the drawings.

The configuration of an X-ray imaging apparatus 100 according to the embodiment of the present invention is now described with reference to FIG. 1. The X-ray imaging apparatus 100 is an example of a "radiographic imaging apparatus" in the claims.

(Configuration of X-Ray Imaging Apparatus)

Figure 1:
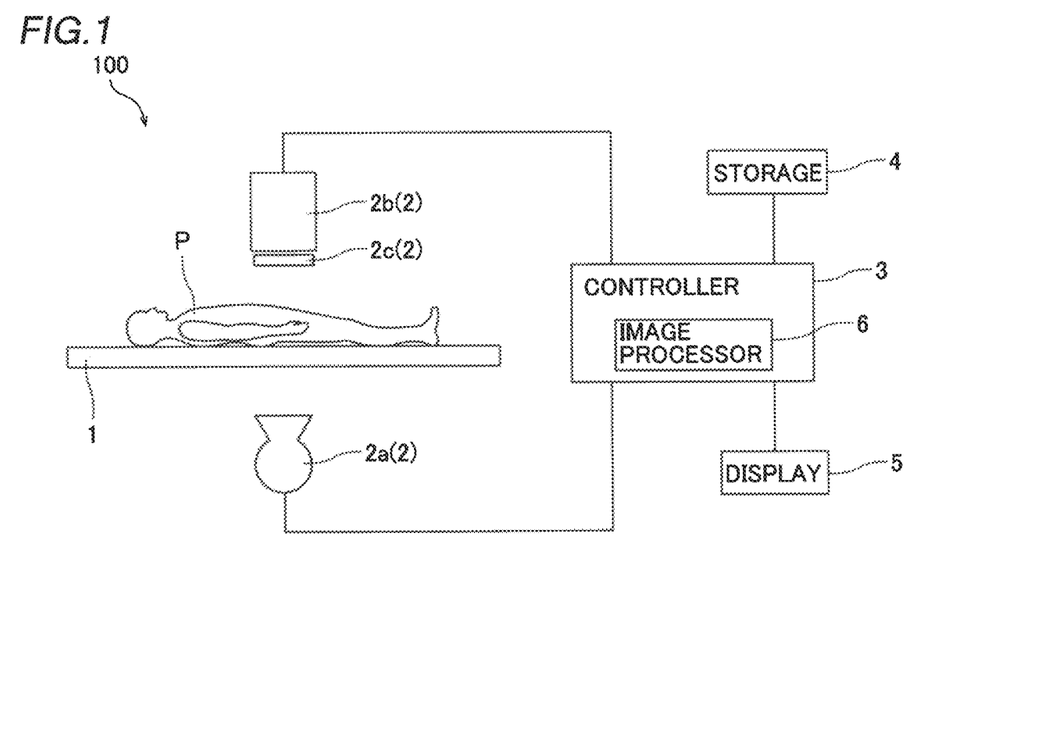
FIG. 1 is a diagram showing the overall configuration of a radiographic imaging apparatus according to an embodiment of the present invention.

As shown in FIG. 1, the X-ray imaging apparatus 100 according to this embodiment includes a table 1 on which a subject P is placed, an imager 2 configured to radiograph the subject P, a controller 3 configured to control various components of the X-ray apparatus 100, a storage 4 configured to store X-ray images etc., and a display 5 configured to display the X-ray images etc.

The imager 2 includes an X-ray source, and includes an X-ray tube device 2a disposed on one side of the table 1 and an X-ray image receptor 2b disposed on the other side of the table 1.

The X-ray tube device 2a includes an X-ray source, and can radiate X-rays when a voltage is applied thereto by an X-ray tube drive (not shown). The X-ray image receptor 2b includes a flat panel detector (FPD) and is configured to be able to detect the X-rays. Thus, the X-ray imaging apparatus 100 can radiograph the subject P by radiating the X-rays with the X-ray tube device 2a in a state in which the subject P is placed on the table 1 and detecting the X-rays transmitted through the subject P with the X-ray image receptor 2b. In the vicinity of the X-ray tube device 2a, a collimator 2c configured to adjust an irradiation field of the X-rays radiated from the X-ray tube device 2a is provided.

The controller 3 is a computer including a central processing unit (CPU), a read only memory (ROM), a random access memory (RAM), etc. The controller 3 includes an image processor 6 capable of generating X-ray images 10 (see FIG. 3) obtained by radiograph the internal structure of the subject P based on detection signals sent from the X-ray image receptor 2b. The X-ray images 10 are examples of a "radiation image" in the claims.

The image processor 6 is a computer including a processor such as a graphics processing unit (GPU) or a field-programmable gate array (FPGA) configured for image processing. The image processor 6 functions as an image processing apparatus by executing an image processing program stored in the storage 4.

Figure 3:
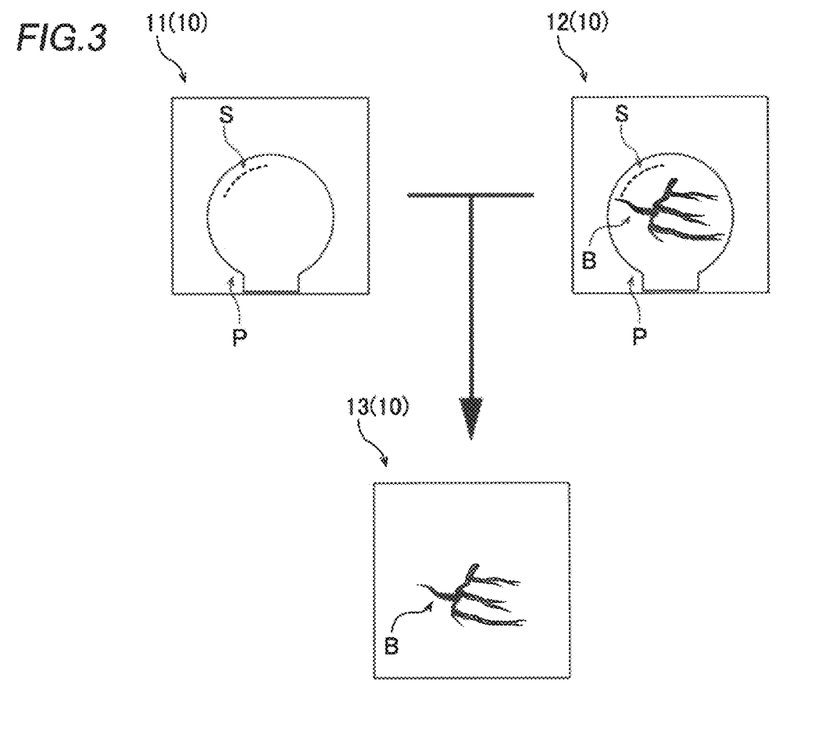
FIG. 3 is a diagram for illustrating generation of a DSA image in which a mask image and a live image are combined.

In this embodiment, as shown in FIG. 3, the image processor 6 is configured to be able to generate a mask image 11, a live image 12, and a digital subtraction angiography (DSA) image 13 as the X-ray images 10. The mask image 11 is an X-ray image 10 obtained by radiographing the subject P in a state in which no contrast medium is administered to the subject P. The live image 12 is an X-ray image 10 obtained by radiographing the subject P in a state in which a contrast medium is administered to the subject P. That is, the mask image 11 and the live image 12 are X-ray images 10 obtained by imaging the same subject P at different times. The DSA image 13 is an X-ray image 10 based on a difference between a pixel value in the mask image 11 and a pixel value in the live image 12. The mask image 11 is an example of a "first image" or a "non-contrast image" in the claims. The live image 12 is an example of a "second image" or a "contrast image" in the claims. The DSA image 13 is an example of a "composite image" in the claims.

As shown in FIG. 3, on the mask image 11, the blood vessels of the subject P are unclearly imprinted (the figure is drawn in such a manner that the blood vessels of the subject P are not imprinted at all) because the subject P is radiographed in a state in which no contrast medium is administered to the subject P. On the other hand, on the live image 12, the blood vessels of the subject P are clearly imprinted as a blood vessel image B because the subject P is radiographed in a state in which the contrast medium is administered to the subject P. The difference between the pixel value in the mask image 11 and the pixel value in the live image 12 is taken (the mask image 11 and the live image 12 are combined) such that the DSA image 13 is generated as an X-ray image 10 on which only the blood vessel image B is imprinted.

The storage 4 includes a non-volatile memory, for example. The storage 4 stores a program used for the processing of the controller 3, and is configured to be able to store the X-ray images 10 (the mask image 11, a deformed image 11a, the live image 12, and the DSA image 13) generated by the image processor 6, for example.

The display 5 is configured as a liquid crystal display, for example. The display 5 is configured to be able to display the X-ray images 10 generated by the image processor 6. In addition, the display 5 is configured to be able to display a plurality of X-ray images 10 as a moving image by continuously displaying the plurality of X-ray images 10.

With the above configuration, the X-ray imaging apparatus 100 can visualize the blood vessels clearly.

As described above, when the DSA image 13 is simply generated based on the difference (pixel value difference) between the pixel value of the mask image 11 and the pixel value of the live image 12, the subject P moves over time between the time of capturing the mask image 11 and the time of capturing the live image 12 such that there is a discrepancy between the position of the subject P in the mask image 11 and the position of the subject P in the live image 12. At this time, artifacts (motion artifacts) due to movement of the subject P are generated in the DSA image 13, and the visibility of the blood vessels is reduced. Before and after the administration of the contrast medium, the subject P may make not only a linear motion such as a parallel motion but also a nonlinear motion such as a twisting motion and a local motion.

Therefore, the image processor 6 is configured to generate the deformed image 11a deformed by correcting a positional deviation between the position of the subject P in the live image 12 and the position of the subject P in the mask image 11 for each pixel 20 (see FIG. 6) (moving the pixel 20 of the mask image 11) based on the pixel value in the live image 12 and the pixel value in the mask image 11 when generating the DSA image 13. That is, the image processor 6 is configured to be able to generate the deformed image 11a based on the mask image 11 and the live image 12. The image processor 6 is configured to generate the DSA image 13 in which the deformed image 11a and the live image 12 are combined. Therefore, in the X-ray imaging apparatus 100, the positional deviation between the subject P in the live image 12 and the subject P in the mask image 11 is corrected for each pixel 20 such that it is possible to significantly reduce or prevent artifacts generated in the DSA image 13 even when the subject P makes a nonlinear motion before and after the administration of the contrast medium.

(Generation of DSA Image in Consideration of Nonlinear Motion of Subject by Image Processor)

First, a rough flow of DSA image generation in consideration of the nonlinear motion of the subject P between the mask image 11 and the live image 12 by the image processor 6 is described with reference to FIG. 4.

Figure 4:
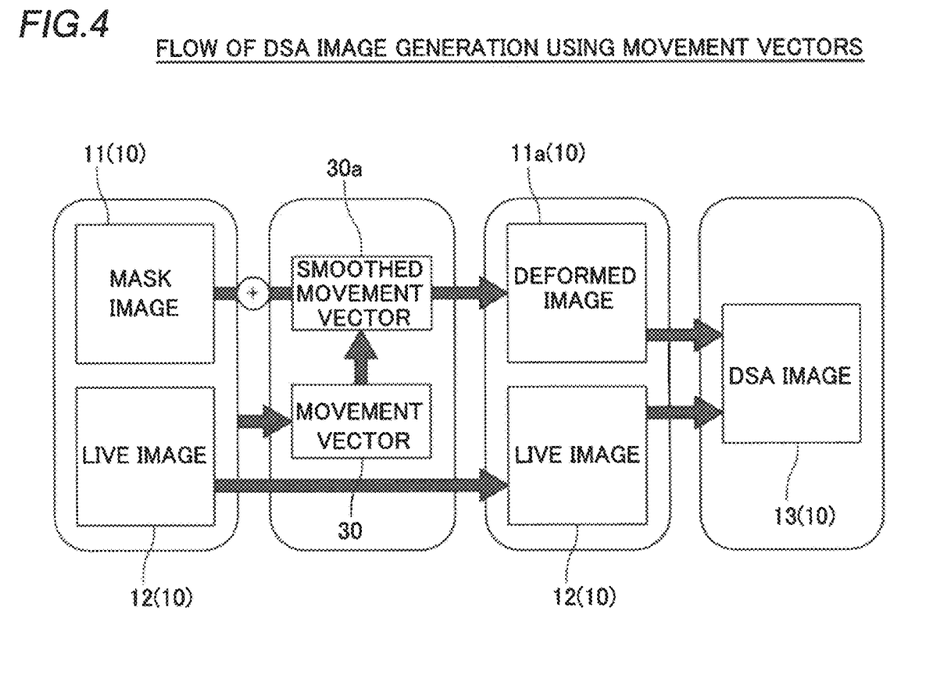
FIG. 4 is a diagram for illustrating a flow of DSA image generation using movement vectors according to the embodiment of the present invention.

As shown in FIG. 4, in the image processor 6, the mask image 11 and the live image 12 are first generated separately. Then, based on the mask image 11 and the live image 12, movement vectors 30 representing the moving directions and the movement amounts of pixels 20 (see FIG. 6) between the mask image 11 and the live image 12 are generated. Then, a smoothed movement vector 30a in which high-frequency components of the movement vectors 30 in the spatial direction have been suppressed is generated. Then, the deformed image 11a obtained by deforming the mask image 11 based on the smoothed movement vector 30a is generated. Then, the DSA image in which the deformed image 11a and the live image 12 are combined is generated. The movement vectors 30 are examples of a "movement map" in the claims. The smoothed movement vector 30a is an example of a "smoothed movement map" in the claims.

(Configuration of Image Processor)

Next, the specific configuration of the image processor 6 is described with reference to FIGS. 2 to 10.

Figure 2:
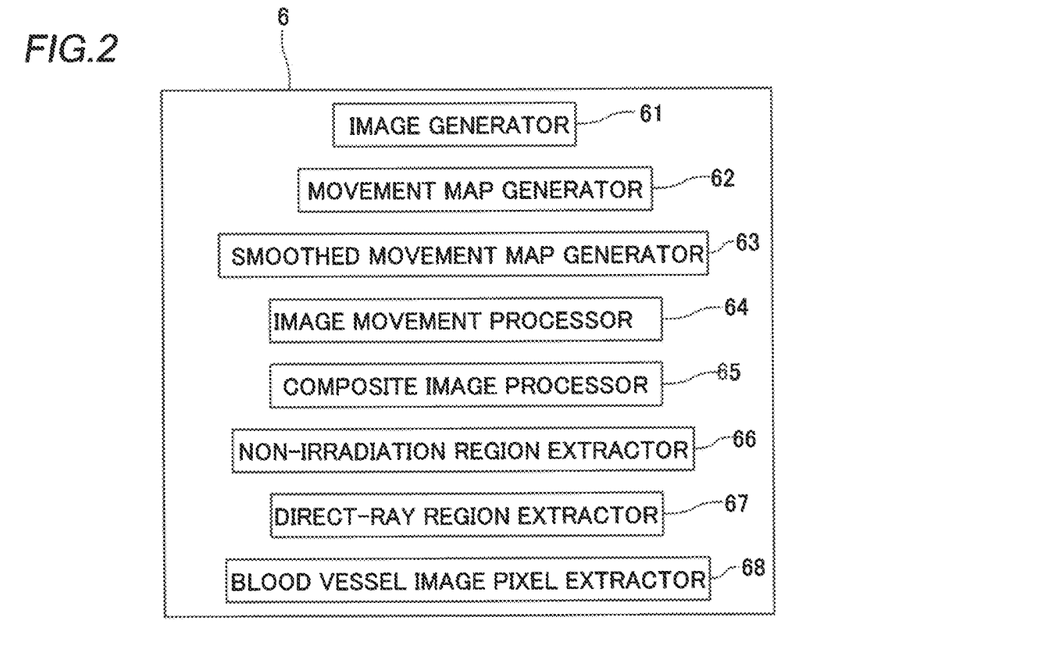
FIG. 2 is a block diagram showing the configuration of an image processor of the radiographic imaging apparatus according to the embodiment of the present invention.

As shown in FIG. 2, the image processor 6 includes an image generator 61, a movement map generator 62, a smoothed movement map generator 63, an image movement processor 64, a composite image processor 65, a non-irradiation region extractor 66, a direct-ray region extractor 67, and a blood vessel image pixel extractor 68.

The image generator 61 generates the X-ray images 10 at a predetermined frame rate by imaging X-ray detection signals sequentially output from the X-ray image receptor 2b. The frame rate is about 15 fps to 30 fps, for example. The X-ray images 10 are images having pixel values of a predetermined number of gradations (such as 10 to 12 bits) in gray scale, for example.

Figure 6:
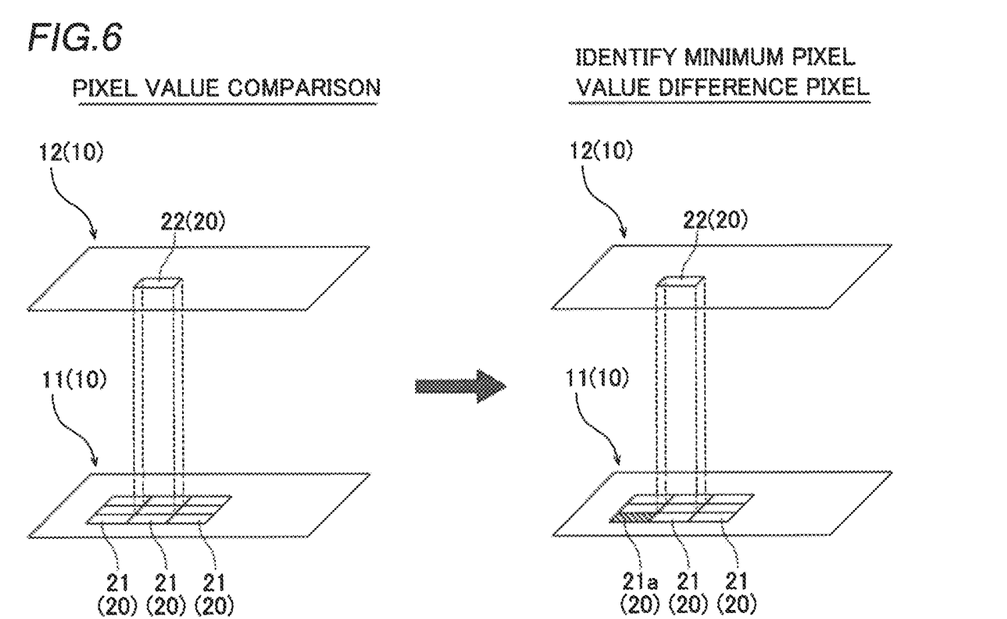
FIG. 6 is a diagram for illustrating a comparison of a pixel of a live image with a pixel of a mask corresponding to that pixel.
Figure 7:
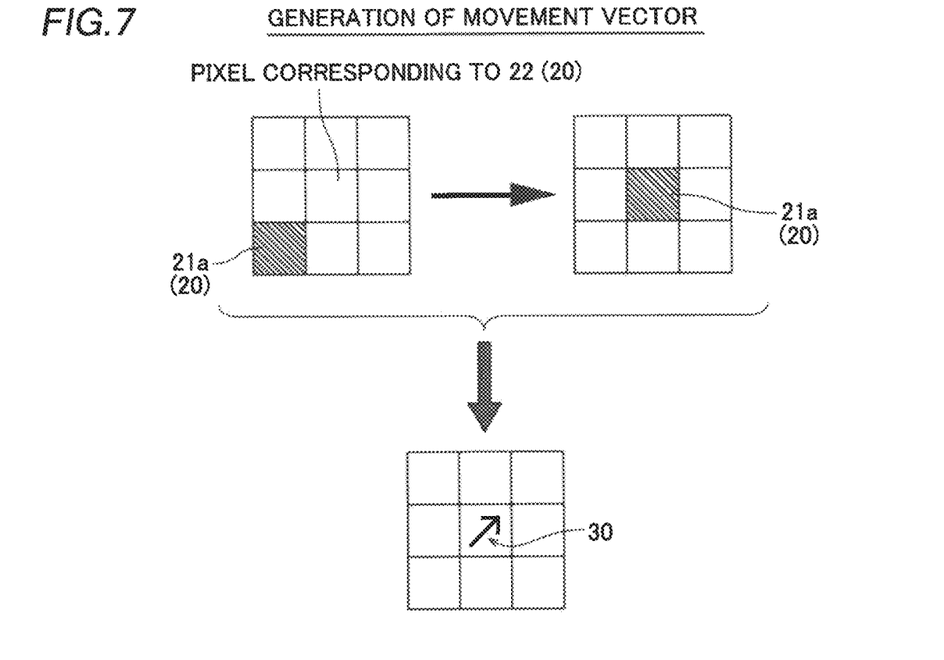
FIG. 7 is a diagram for illustrating generation of a movement vector.

As shown in FIGS. 6 and 7, the movement map generator 62 is configured to generate the movement vector 30 representing the moving direction and the movement amount of a pixel 21 of the mask image 11 based on pixel value differences between a pixel value of a pixel 22 of the live image 12 and pixel values of the pixel 21 of the mask image 11 corresponding to that pixel 22 and pixels 21 belonging to a predetermined surrounding region. Specifically, the movement map generator 62 is configured to generate the movement vector 30 representing the moving direction and the movement amount of the pixel 21 of the mask image 11 based on the pixel value of the pixel 22 of the live image 12 and a pixel value of a minimum pixel value difference pixel 21a, which is a pixel 21 of the mask image 11 having the smallest pixel value difference with respect to the pixel 22 of the live image 12.

More specifically, as shown in FIG. 6, the movement map generator 62 compares the pixel value of the pixel 22 of the live image 12 with the pixel values of a total of nine pixels 21 including the pixel 21 of the mask image 11 corresponding to (at the same coordinate as) that pixel 22 and the pixels 21 in the predetermined surrounding region around the corresponding pixel 21 (a total of eight pixels 21 including upper, upper right, right, lower right, lower, lower left, left, and upper left pixels with respect to the corresponding pixel 21). Then, the movement map generator 62 identifies a pixel (minimum pixel value difference pixel 21a) having the smallest difference in pixel value from that pixel 22 of the live image 12 among the nine pixels 21 of the mask image 11. The pixel value is a quantitative value that varies depending on the position of the subject P, and thus the pixel value serves as an index of the position of the subject P in the live image 12 and the mask image 11. Therefore, as described above, comparing that pixel 22 of the live image 12 with the nine pixels 21 of the mask image 11 at the same coordinate as that of that pixel 22 and in the surrounding region corresponds to checking the positional deviation of the mask image 11 with respect to the pixel 22 of the live image 12. Furthermore, the minimum pixel value difference pixel 21a of the mask image 11 can be regarded as a pixel 20 that is most likely to be positionally deviated from a position corresponding to the pixel 22 of the live image 12. Then, as shown in FIG. 7, the movement map generator 62 sets the moving direction and the movement amount of the minimum pixel value difference pixel 21a in the case in which the minimum pixel value difference pixel 21a is moved to the position of the pixel 21 of the mask image 11 corresponding to (at the same coordinate as) the pixel 22 of the live image 12 to a movement vector 30 corresponding to the pixel 21 of the mask image 11.

Figure 9:
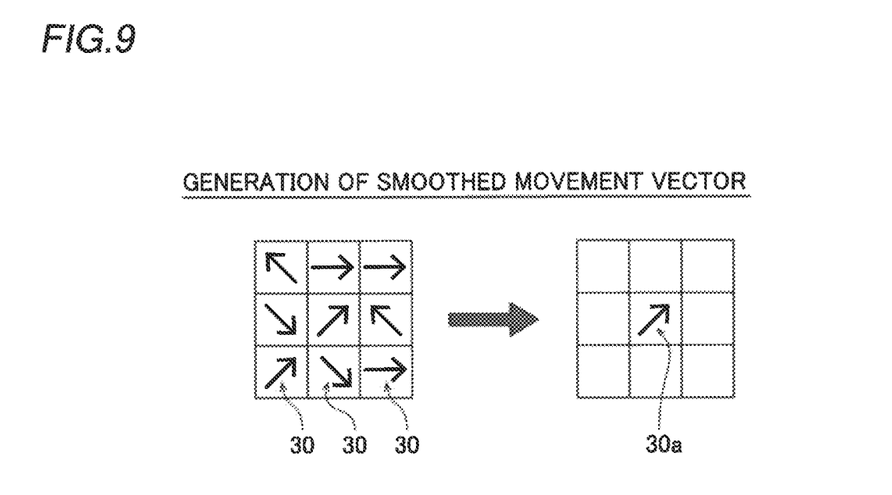
FIG. 9 is a diagram for illustrating generation of a smoothed movement vector.

As shown in FIG. 9, the smoothed movement map generator 63 is configured to generate the smoothed movement vector 30a by suppressing the high-frequency components of the movement vectors 30 in the spatial direction.

Figure 10:
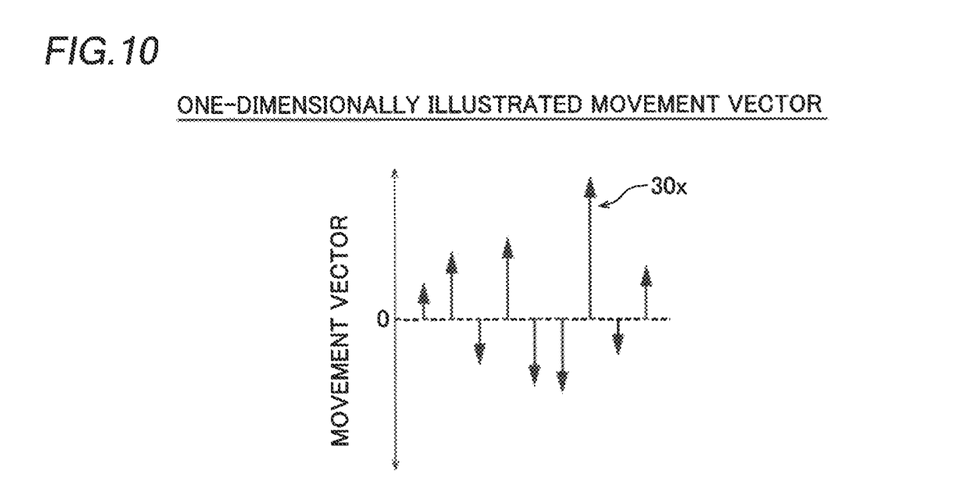
FIG. 10 is a diagram for illustrating suppression of high-frequency components by smoothing of the movement vectors.

Specifically, as shown in FIG. 9, the smoothed movement map generator 63 calculates the smoothed movement vector 30a obtained by smoothing the movement vectors 30 with the pixel 21 of the mask image 11 and the pixels 21 around the pixel 21 of the mask image 11 for each pixel 21 of the mask image 11. That is, the smoothed movement map generator 63 calculates the smoothed movement vector 30a obtained by smoothing the movement vector 30 associated with each pixel 21 of the mask image 11 with the pixel 21 and the surrounding eight pixels 21. Note that the smoothing can be performed by simply averaging movement vectors 30 with the nine pixels 21, for example. Thus, as shown in FIG. 10, even when an excessively different movement vector 30 (movement vector 30x) is included in the nine pixels 21, the movement vectors 30 are averaged such that the influence of the excessively different movement vector 30x is reduced. Consequently, the high-frequency components of the movement vectors 30 in the spatial direction are suppressed. In FIG. 9, due to space constraints, the smoothed movement vector 30a is drawn as a vector having the same direction and magnitude as those of the movement vector 30 before smoothing. Note that the smoothing is not limited to the case in which the movement vectors 30 are simply averaged with the nine pixels 21. For example, after the movement vectors 30 of the nine pixels 21 are graphed as the movement amount for each moving direction, the high-frequency components are extracted by performing Fourier transform. Then, the high-frequency components are removed such that the high-frequency components of the movement vectors 30 in the spatial direction may be suppressed.

The smoothed movement map generator 63 associates the generated smoothed movement vector 30a with the pixel 21 of the mask image 11 corresponding to the pixel 22 of the live image 12. Then, the smoothed movement map generator 63 performs this association with respect to all the pixels 21 of the mask image 11 such that the smoothed movement vectors 30a are respectively associated with all the pixels 21 of the mask image 11.

As shown in FIG. 4, the image movement processor 64 is configured to move the pixel 21 of the mask image 11 based on the smoothed movement vector 30a and generate the deformed image 11a.

Specifically, the image movement processor 64 moves the pixel 21 of the mask image 11 based on the smoothed movement vector 30a. That is, the image movement processor 64 moves a certain pixel 21 on the mask image 11 by the moving direction and the movement amount of the smoothed movement vector 30a associated with the pixel 21 in the mask image 11. This movement of the pixel 21 based on the smoothed movement vector 30a is performed for each pixel 21 of the mask image 11 over the entire mask image 11 such that the mask image 11 becomes the deformed image 11a (a mask image on which positional deviation correction has been performed).

Figure 8:
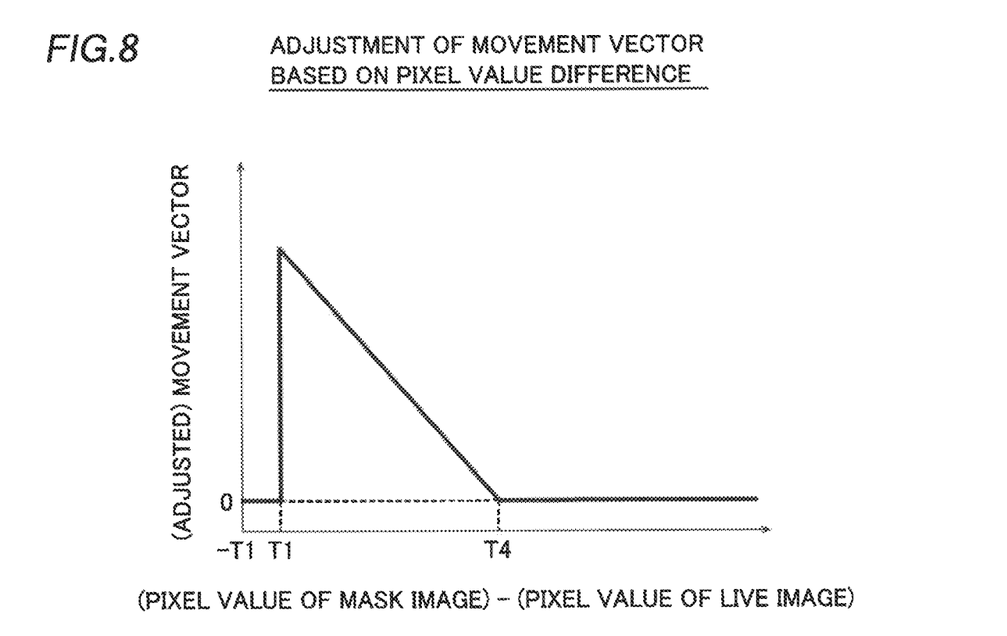
FIG. 8 is a diagram for illustrating adjustment of the movement amount (movement vector) of the pixel of the mask image based on a pixel value difference between a pixel value of the pixel of the live image and a pixel value of the pixel of the mask image corresponding to that pixel of the live image.

As shown in FIG. 8, the image movement processor 64 is configured to set the movement amount of the pixel 21 of the mask image 11 (the magnitude of the movement vector 30) to 0 when the pixel value difference between the pixel value of the pixel 22 of the live image 12 and the pixel value of the pixel 21 of the mask image 11 corresponding to that pixel 22 is equal to or less than a first threshold T1. That is, when the pixel value difference between the pixel 22 of the live image 12 and the pixel 21 of the mask image 11 corresponding to that pixel 22 is equal to or less than the preset first threshold T1, the image movement processor 64 does not move the pixel 21 of the mask image 11, assuming that there is almost no positional deviation between the pixel 22 of the live image 12 and the pixel 21 of the mask image 11 corresponding to that pixel 22.

Figure 5:
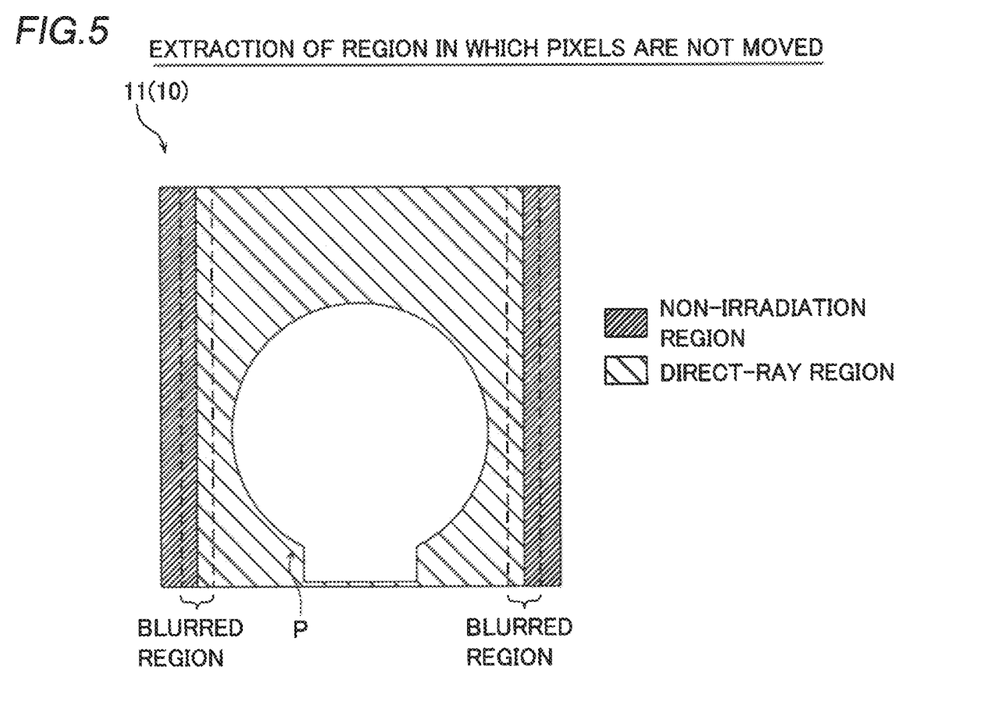
FIG. 5 is a diagram for illustrating a non-irradiation region and a direct-ray region.

As shown in FIG. 5, the image movement processor 64 is configured to set the movement amount of the pixel 21 of the mask image 11 in a non-irradiation region extracted by the non-irradiation region extractor 66 to 0. Specifically, the image movement processor 64 causes the movement map generator 62 not to generate the movement vector 30 for the pixel 21 of the mask image 11 in the non-irradiation region extracted by the non-irradiation region extractor 66 so as to exclude the non-irradiation region from a target on which correction processing of positional deviation correction is to be performed (determine excluded pixels). The non-irradiation region refers to a region in which an X-ray irradiation field is adjusted by the collimator (not shown), and refers to a region in the X-ray image 10 in which substantially nothing is captured.

The image movement processor 64 is configured to set the movement amounts of the pixels 21 in a direct-ray region of the mask image 11 extracted by the direct-ray region extractor 67 to 0. Specifically, the image movement processor 64 causes the movement map generator 62 not to generate the movement vectors 30 for the pixels 21 in the direct-ray region of the mask image 11 extracted by the direct-ray region extractor 67 so as to exclude the direct-ray region from the target on which correction processing of positional deviation correction is to be performed (determine excluded pixels). The direct-ray region refers to a region in which the X-rays radiated from the X-ray tube device 2a are directly detected by the X-ray image receptor 2b.

As shown in FIG. 8, the image movement processor 64 is configured to set the movement amount of the pixel 21 of the mask image 11 corresponding to the pixel 22 that constitutes the blood vessel image B extracted by the blood vessel image pixel extractor 68 to 0. Specifically, the image movement processor 64 does not move the pixel 21 of the mask image 11 by setting the magnitude of the movement vector 30 generated by the movement map generator 62 for the pixel 21 of the mask image 11 corresponding to the pixel 22 determined as the pixel 22 that constitutes the blood vessel image B extracted by the blood vessel image pixel extractor 68 to 0.

As shown in FIG. 8, the image movement processor 64 is configured to gradually increase the movement amount of the pixel 21 of the mask image 11 as the pixel value difference between the pixel value of the pixel 22 that constitutes the live image 12 and the pixel value of the pixel 21 of the mask image 11 corresponding to that pixel 22 decreases when that pixel value difference is smaller than a fourth threshold T4. Specifically, the image movement processor 64 adjusts the movement amount (the magnitude of the movement vector 30) of the pixel 21 of the mask image 11 according to whether or not the pixel 22 of the live image 12 is likely to be the pixel 22 that constitutes the blood vessel image B when the pixel value difference between the pixel value of the pixel 22 that constitutes the live image 12 and the pixel value of the pixel 21 of the mask image 11 corresponding to that pixel 22 is smaller than the fourth threshold T4 and the pixel value is a value close to the fourth threshold T4.

The image movement processor 64 is configured not to set, to 0, the movement amount of a pixel 21 corresponding to a pixel 22 having a pixel value equal to or less than a fifth threshold among the pixels 21 of the mask image 11 corresponding to the pixels 22 of the live image 12 determined as the pixels 22 that constitute the blood vessel image B by the blood vessel image pixel extractor 68. Specifically, the image movement processor 64 causes the movement map generator 62 to generate the movement vector 30 for the pixel 21 of the mask image 11 corresponding to the pixel 22 having a pixel value equal to or less than the fifth threshold and being unlikely to be the pixel that constitutes the blood vessel image B even when determining that pixel 22 of the live image 12 as the pixel 22 that constitutes the blood vessel image B by the blood vessel image pixel extractor 68. Note that in the mask image 11 that does not contain the blood vessel image B, a portion S (see FIG. 3) having a relatively low pixel value (equal to or less than the fifth threshold) is regarded as a portion (a portion of the skeleton, for example) other than a portion corresponding to the blood vessel image B of the subject P.

The image movement processor 64 is configured to average pixel values of a plurality of pixels 21 and correct the smoothed movement vector 30a when the pixel 21 is moved based on the smoothed movement vector 30a such that the plurality of pixels 21 overlap with each other. Specifically, when in a movement destination of the pixel 21 based on the smoothed movement vector 30a, the movement amount of the smoothed movement vector 30a is 0 such that there is no movement of the pixel 21, and when movement destinations of the plurality of pixels 21 based on the smoothed movement vectors 30a are the same, a pixel value obtained by averaging the pixel values of the plurality of overlapping pixels 21 is set as a pixel value of the movement destination.

The image movement processor 64 is configured to correct the smoothed movement vector 30a by interpolating a blank pixel 21 by pixels 21 around the blank pixel 21 when the pixel 21 is moved based on the smoothed movement vector 30a such that the blank pixel 21 is generated. Specifically, when the blank pixel 21 is generated because another pixel 21 has not moved to a movement source of the pixel 21 based on the smoothed movement vector 30a, the blank pixel 21 is interpolated by the surrounding (eight neighboring) pixels 21 adjacent to the blank pixel 21 by a well-known image interpolation method.

The image movement processor 64 is configured to correct the smoothed movement vector 30a by moving the pixel value of the pixel 21 of the mask image 11 by a proportion corresponding to the smoothed movement vector 30a when the pixel 21 is moved based on the smoothed movement vector 30a and when the smoothed movement vector 30a is not an integer value. Specifically, for example, when the direction and magnitude of the smoothed movement vector 30a are a right direction and 0.5, respectively, a pixel value 0.5 times a pixel value of a pixel 21 on the left of the pixel 21 associated with the smoothed movement vector 30a is moved to the pixel 21 associated with the smoothed movement vector 30a. A pixel value corresponding to the proportion of the pixel value of the pixel 21 on the left of the pixel 21 associated with the smoothed movement vector 30a that is not moved (0.5 times (1 time−0.5 times) the pixel value of the left pixel 21) is not moved from the position of the left pixel 21.

The composite image processor 65 is configured to generate the DSA image 13 in which the deformed image 11a and the live image 12 are combined. Specifically, as shown in FIG. 4, the composite image processor 65 combines the deformed image 11a based on the movement vector 30 (smoothed movement vector) generated based on the mask image 11 and the live image 12 and the live image 12.

As shown in FIG. 4, the non-irradiation region extractor 66 is configured to extract a non-irradiation region of radiation generated by the operation of the collimator in the mask image 11. The non-irradiation region extractor 66 is configured to determine a region of the mask image 11 outside boundary pixels as the non-irradiation region, defining pixels 21 adjacent to the outside in the vicinity of the top, bottom, left, and right edges of the mask image 11, each of which has a pixel value equal to or greater than a second threshold, as the boundary pixels. Specifically, when a pixel value difference between adjacent pixels 21 in the vicinity of the top, bottom, left, and right of the X-ray image 10 is equal to or greater than the second threshold, the non-irradiation region extractor 66 determines a region in which the adjacent pixels 21 are located as a boundary between an irradiation region with a high pixel value and a non-irradiation region with a pixel value close to 0 (zero). That is, the non-irradiation region extractor 66 extracts the boundary between the irradiation region and the non-irradiation region by calculating the difference between the pixel values of the adjacent pixels 21 (first derivative calculation). In FIG. 4, for convenience, collimator regions are drawn only on the left and right sides of the X-ray image 10.

The image processor 6 is configured to perform blurring processing, defining the boundary between the non-irradiation region of X-rays and the region (irradiation region) inside the non-irradiation region as a blurred region. The blurring processing aims to make the boundary between the non-irradiation region and the irradiation region less noticeable because in the DSA image 13 in which the blood vessels are clearly visualized, a boundary line that appears between the non-irradiation region and the irradiation region does not look good, for example. The blurring processing is performed by smoothing pixel values of the boundary pixels with pixel values of pixels adjacent to the boundary pixels, for example.

As shown in FIG. 4, the direct-ray region extractor 67 is configured to extract the direct-ray region in the mask image 11. The direct-ray region extractor 67 is configured to determine a region of the mask image 11 in which the pixel values of the pixels 21 that constitute the mask image 11 are equal to or greater than a third threshold as the direct-ray region. Specifically, the direct-ray region corresponds to a portion of the X-ray image 10 in which the subject P is not present. Therefore, the direct-ray region can be recognized as a pixel value equal to or greater than a predetermined third threshold close to the upper limit ($2^n$ in the case of an n-bit image) of the pixel value.

The blood vessel image pixel extractor 68 is configured to extract the pixels 22 that constitute the blood vessel image B in the live image 12. The blood vessel image pixel extractor 68 is configured to determine the pixels 22 that constitute the live image 12 as the pixels 22 that constitute the blood vessel image B when the pixel value differences between the pixel values of the pixels 22 that constitute the live image 12 and the pixel values of the pixels 21 of the mask image 11 corresponding to those pixels 22 are equal to or greater than the fourth threshold T4 (see FIG. 4).

The image processor 6 is configured to perform blurring processing, defining the boundary between the non-irradiation region of X-rays and the region (irradiation region) inside the non-irradiation region as a blurred region. The blurring processing aims to make the boundary between the non-irradiation region and the irradiation region less noticeable because in the DSA image 13 in which the blood vessels are clearly visualized, a boundary line that appears between the non-irradiation region and the irradiation region does not look good, for example. The blurring processing is performed by smoothing the pixel values of the boundary pixels with the pixel values of the pixels adjacent to the boundary pixels, for example.

(Flow of Composite Image Generation Processing Using Movement Vectors)

Figure 11:
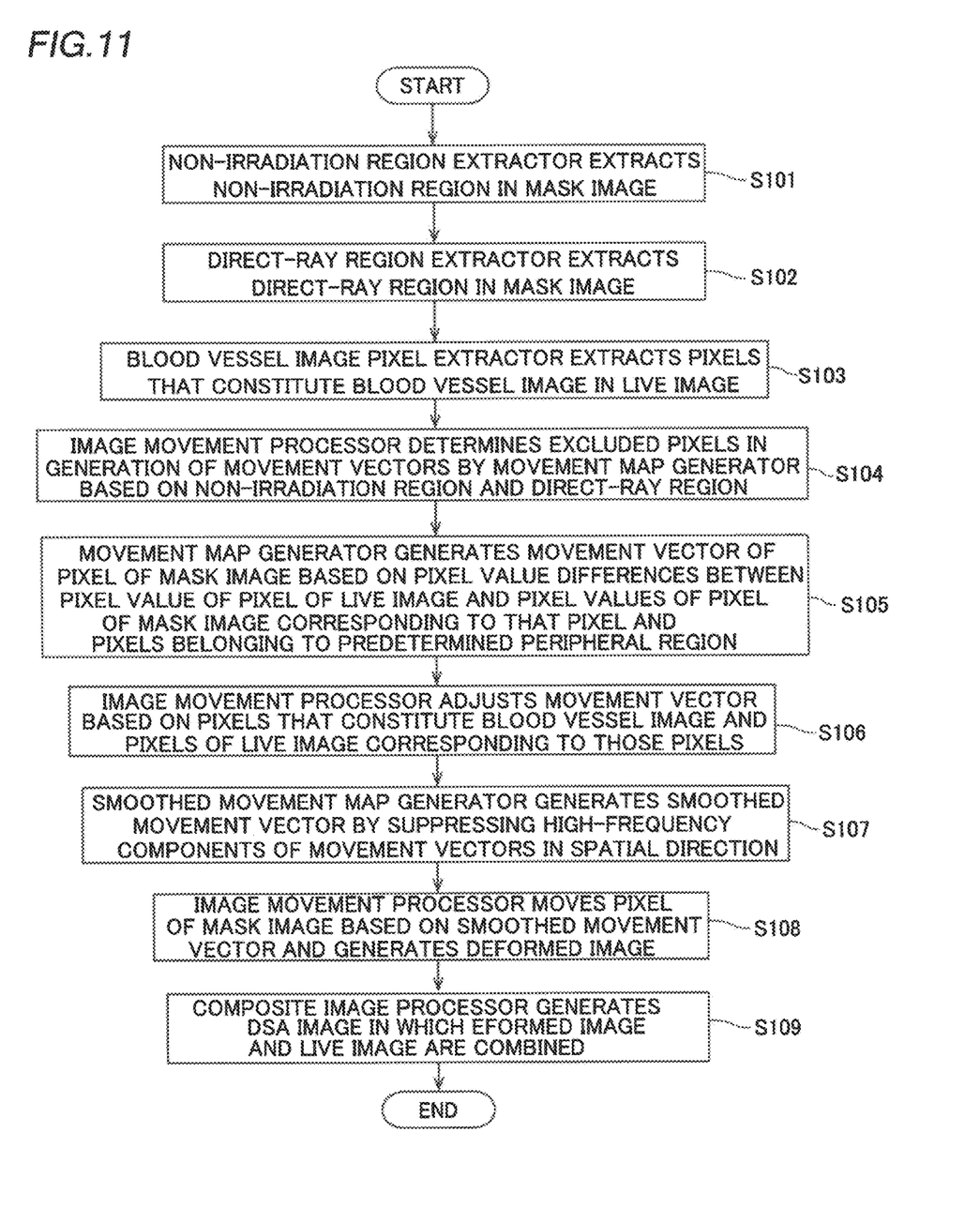
FIG. 11 is a flowchart of DSA image generation processing using the movement vectors.

A flow of DSA image 13 generation processing using the movement vectors 30 by the image processor 6 is now described with reference to FIG. 11. It is assumed that the mask image 11 and the live image 12 are generated prior to this flow.

First, in step S101, the non-irradiation region extractor 66 extracts the non-irradiation region in the mask image 11.

Then, in step S102, the direct-ray region extractor 67 extracts the direct-ray region in the mask image 11.

Then, in step S103, the blood vessel image pixel extractor 68 extracts the pixels 22 that constitute the blood vessel image B in the live image 12.

Then, in step S104, the image movement processor 64 determines excluded pixels in generation of the movement vectors 30 by the movement map generator 62 based on the non-irradiation region and the direct-ray region.

Then, in step S105, the movement map generator 62 generates the movement vector 30 of the pixel 21 of the mask image 11 based on the pixel value differences between the pixel value of the pixel 22 of the live image 12 and the pixel values of the pixel 21 of the mask image 11 corresponding to that pixel 22 and the pixels 21 belonging to the predetermined surrounding region.

Then, in step S106, the image movement processor 64 adjusts the movement vector 30 based on the pixel values of the pixels 22 that constitute the blood vessel image B and the pixel values of the pixels 21 of the live image 12 corresponding to those pixels 22.

Then, in step S107, the smoothed movement map generator 63 generates the smoothed movement vector 30a by suppressing the high-frequency components of the movement vectors 30 in the spatial direction.

Then, in step S108, the image movement processor 64 moves the pixel 21 of the mask image 11 based on the smoothed movement vector 30a and generates the deformed image 11a.

Then, in step S109, the composite image processor 65 generates the DSA image 13 in which the deformed image 11a and the live image 12 are combined.

In the above flow, the order of step S101, step S102, and step S103 can be interchanged.

Advantages of Embodiment

In this embodiment, the following advantages are obtained.

In this embodiment, as described above, the X-ray imaging apparatus 100 is configured to generate the movement vectors 30 of the pixels 21 belonging to the mask image 11 based on the mask image 11 and the live image 12 captured at the different times, and move the pixels 21 of the mask image 11 based on the movement vectors 30 and generate the deformed image 11a. Accordingly, the movement vector 30 can be generated for each pixel 21 belonging to the mask image 11, and the deformed image 11a can be generated, and thus unlike the case in which the entire region is uniformly moved in parallel and the deformed image 11a is generated, the deformed image 11a in which only a partial region in the mask image 11 has been deformed can be generated. Furthermore, as described above, the deformed image 11a is generated based on the smoothed movement vector 30a in which the high-frequency components of the movement vectors 30 in the spatial direction have been suppressed. Thus, even when an error occurs in the movement vector 30 due to generation of the movement vector 30 for each pixel 21, the influence of the error can be reduced by suppressing the high-frequency components in the spatial direction. Consequently, it is possible to appropriately combine the two images captured at the different times in consideration of not only the linear motion but also the nonlinear motion of the subject P between the two images.

In this embodiment, as described above, the movement map generator 62 is configured to generate the movement vectors 30 representing the moving directions and the movement amounts of the pixels 21 of the mask image 11 based on the pixel value differences between the pixel value of the pixel 22 of the live image 12 and the pixel values of the pixel 21 of the mask image 11 corresponding to that pixel 22 and the pixels 21 belonging to the predetermined surrounding region. Accordingly, the movement vectors 30 representing the moving direction and the movement amount of each pixel 21 belonging to the mask image 11 can be easily generated based on the mask image 11 and the live image 12 serving as an index of a specific position of the subject P.

In this embodiment, as described above, the movement map generator 62 is configured to generate the movement vector 30 representing the moving direction and the movement amount of the pixel 21 of the mask image 11 based on the pixel value of the pixel 22 of the live image 12 and the pixel value of the minimum pixel value difference pixel 21a, which is the pixel 21 of the mask image 11 having the smallest pixel value difference with respect to the pixel 22 of the live image 12. Accordingly, the minimum pixel value difference pixel 21a of the mask image 11 has the highest probability of being a pixel 21 used as a reference for the pixel 22 of the live image 12 among the pixel 21 of the mask image 11 and the pixels 21 belonging to the predetermined surrounding region, and thus the movement vector 30 can be accurately generated by using the minimum pixel value difference pixel 21a.

In this embodiment, as described above, the image movement processor 64 is configured to set the movement amount of the pixel 21 of the mask image 11 to 0 when the pixel value difference between the pixel value of the pixel 22 of the live image 12 and the pixel value of the pixel 21 of the mask image 11 corresponding to that pixel 22 is equal to or less than the first threshold T1. Accordingly, it is possible to significantly reduce or prevent movement of a pixel 21 of the mask image 11 that does not need to be moved due to almost no movement of the pixel 22 of the live image 12 and the pixel 21 of the mask image 11 corresponding to that pixel 22.

In this embodiment, as described above, the X-ray imaging apparatus 100 includes the collimator configured to narrow down an irradiation region of radiation to the subject P, and the non-irradiation region extractor 66 configured to extract the non-irradiation region of radiation generated by the operation of the collimator in the mask image 11, and the image movement processor 64 is configured to set the movement amounts of the pixels 21 of the mask image 11 in the non-irradiation region extracted by the non-irradiation region extractor 66 to 0. Accordingly, it is possible to significantly reduce or prevent movement of the pixels 21 in the non-irradiation region the mask image 11, which are not irradiated with radiation and that do not need to be moved. Consequently, it is possible to effectively reduce the control burden on the image movement processor 64 when the non-irradiation region is large.

In this embodiment, as described above, the non-irradiation region extractor 66 is configured to determine the region of the mask image 11 outside the boundary pixels as the non-irradiation region, defining the pixels 21 adjacent to the outside in the vicinity of the top, bottom, left, and right edges of the mask image 11, each of which has a pixel value equal to or greater than the second threshold, as the boundary pixels. Accordingly, when the pixel value difference between the adjacent pixels 21 in the vicinity of the top, bottom, left, and right edges of the image is equal to or greater than the second threshold, the region in which the adjacent pixels 21 are located is likely to be the boundary between the irradiation region with a high pixel value and the non-irradiation region with a pixel value close to 0 (zero), and thus the pixels 21 in the non-irradiation region of the mask image 11 can be easily determined.

In this embodiment, as described above, the X-ray imaging apparatus 100 includes the direct-ray region extractor 67 configured to extract the direct-ray region in the mask image 11, and the image movement processor 64 is configured to set the movement amounts of the pixels 21 in the direct-ray region of the mask image 11 extracted by the direct-ray region extractor 67 to 0. Accordingly, it is possible to significantly reduce or prevent movement of the pixels 21 in the direct-ray region, which is a region in the mask image 11 in which the subject P is not present, that do not need to be moved. Consequently, it is possible to effectively reduce the control burden on the image movement processor 64 when the direct-ray region is large.

In this embodiment, as described above, the direct-ray region extractor 67 is configured to determine the region of the mask image 11 in which the pixel values of the pixels 21 that constitute the mask image 11 are equal to or greater than the third threshold as the direct-ray region. Accordingly, the region of the mask image 11 in which the pixel values of the pixels 21 are equal to or greater than the third threshold is likely to be the direct-ray region in which radiation is directly detected without passing through the subject P, and thus the pixels 21 in the direct-ray region of the mask image 11 can be easily determined.

In this embodiment, as described above, the mask image 11 is a non-contrast image that is a radiation image (X-ray image 10) obtained by imaging the subject P in a state in which no contrast medium is administered to the blood vessels of the subject P, and the live image 12 is a contrast image that is a radiation image (X-ray image 10) obtained by imaging the subject P in a state in which the contrast medium is administered to the blood vessels of the subject P. Accordingly, the contrast image (live image 12) and the non-contrast image (mask image 11) captured at the different times can be combined in consideration of not only the linear motion but also the nonlinear motion of the subject P between the contrast image (live image 12) and the non-contrast image (mask image 11).

In this embodiment, as described above, the X-ray imaging apparatus 100 includes the blood vessel image pixel extractor 68 configured to extract the pixel 22 that constitutes the blood vessel image B in the live image 12, and the image movement processor 64 is configured to set the movement amount of the pixel 21 of the mask image 11 corresponding to the pixel 22 that constitutes the blood vessel image B to 0. Accordingly, it is possible to significantly reduce or prevent blurriness of the blood vessel image B in the DSA image 13 in which the live image 12 and the mask image 11 are combined due to movement of the pixel 21 of the mask image 11 corresponding to the pixel 22 that constitutes the blood vessel image B.

In this embodiment, as described above, the blood vessel image pixel extractor 68 is configured to determine the pixel 22 that constitutes the live image 12 as the pixel 22 that constitutes the blood vessel image B when the pixel value difference between the pixel value of the pixel 22 that constitutes the live image 12 and the pixel value of the pixel 21 of the mask image 11 corresponding to that pixel 22 is equal to or greater than the fourth threshold T4. Accordingly, when the pixel value difference between the pixel value of the pixel 22 that constitutes the live image 12 and the pixel value of that pixel 21 of the mask image 11 is equal to or greater than the fourth threshold T4, that pixel 22 of the live image 12 is likely to be the pixel that constitutes the blood vessel image B, and thus the pixel 22 of the blood vessel image B in the live image 12 can be easily determined.

In this embodiment, as described above, the image movement processor 64 is configured to gradually increase the movement amount of the pixel 21 of the mask image 11 as the pixel value difference between the pixel value of the pixel 22 that constitutes the live image 12 and the pixel value of the pixel 21 of the mask image 11 corresponding to that pixel 22 decreases when that pixel value difference is smaller than the fourth threshold T4. Accordingly, because the pixels 22 that constitute the blood vessel image B are shaded, depending on the possibility that the pixel 22 of the live image 12 is not the pixel 22 that constitutes the blood vessel image B, the movement amount of the pixel 21 of the mask image 11 corresponding to that pixel 22 can be adjusted.

In this embodiment, as described above, the image movement processor 64 is configured not to set, to 0, the movement amount of the pixel 21 corresponding to the pixel 22 having a pixel value equal to or less than the fifth threshold among the pixels 21 of the mask image 11 corresponding to the pixels 22 of the live image 12 determined as the pixels 22 that constitute the blood vessel image B by the blood vessel image pixel extractor 68. Accordingly, it is possible to significantly reduce or prevent generation of the deformed image 11a without movement of the pixel 21 of the mask image 11 corresponding to the pixel 22 having a pixel value equal to or less than the fifth threshold and being unlikely to be the pixel 22 that constitutes the blood vessel image B among the pixels 22 that constitute the live image 12 and have been determined as the pixels 22 that constitute the blood vessel image B.

MODIFIED EXAMPLES

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the example in which the image movement processor 64 generates the deformed image 11a based on the smoothed movement vector 30a obtained by averaging the movement vectors 30 with the pixel 21 of the mask image 11 and the eight neighboring pixels 21 around the pixel 21 of the mask image 11 for each pixel 21 of the mask image 11 has been shown in the aforementioned embodiment, the present invention is not limited to this. In the present invention, the image movement processor 64 may generate the deformed image 11a based on the movement vectors 30 before averaging without using the smoothed movement vector 30a.

While the example in which the movement map generator 62 calculates the movement vector 30 based on the pixel value differences that are the differences between the pixel value of the pixel 22 of the live image 12 and the pixel values of the pixel 21 of the mask image 11 corresponding to the pixel 22 of the live image 12 and the eight neighboring pixels 21 around the pixel 21 of the mask image 11 (nine pixels in total) has been shown in the aforementioned embodiment, the present invention is not limited to this. In the present invention, the movement map generator 62 may calculate the movement vector 30 based on pixel value differences with the number of pixels 21 other than nine. In this case, for example, the number of pixels 21 may be reduced to five including the pixel 21 of the mask image 11 and four neighboring pixels 21 in the upper, lower, left, and right directions of the pixel 21 of the mask image 11. Alternatively, the number of pixels 21 may be increased to twenty-five including the pixel 21 of the mask image 11, the eight neighboring pixels 21, and twelve neighboring pixels 21 around the eight neighboring pixels 21 (three pixels 21 in each of the upper, lower, left, and right directions and pixels 21 in the upper right, lower right, lower left, and upper left directions), for example. Thus, the movement vector 30 is calculated based on pixel value differences with a large number of pixels 21 such that the accuracy of calculating the movement vector 30 can be improved.

While the example in which the image movement processor 64 generates the deformed image 11a based on the smoothed movement vector 30a obtained by averaging the movement vectors 30 with the pixel 21 of the mask image 11 and the eight neighboring pixels 21 around the pixel 21 of the mask image 11 (nine pixels in total) for each pixel 21 of the mask image 11 has been shown in the aforementioned embodiment, the present invention is not limited to this. In the present invention, the image movement processor 64 may generate the deformed image 11a based on the smoothed movement vector 30a obtained by averaging the number of pixels 21 other than nine. In this case, for example, the number of pixels 21 may be reduced to five including the pixel 21 of the mask image 11 and four neighboring pixels 21 in the upper, lower, left, and right directions of the pixel 21 of the mask image 11. Alternatively, the number of pixels 21 may be increased to twenty-five including the pixel 21 of the mask image 11, the eight neighboring pixels 21, and twelve neighboring pixels 21 around the eight neighboring pixels 21 (three pixels 21 in each of the upper, lower, left, and right directions and pixels 21 in the upper right, lower right, lower left, and upper left directions), for example. Thus, the deformed image 11a is generated based on the smoothed movement vector 30a obtained by averaging pixel value differences with a large number of pixels 21 such that the accuracy of generating the deformed image 11a can be improved.

While the example in which the non-irradiation region extractor 66 is configured to determine the region in which the adjacent pixels 21 are located as the boundary between the irradiation region with a high pixel value and the non-irradiation region with a pixel value close to 0 (zero) when the pixel value difference between the adjacent pixels 21 in the vicinity of the top, bottom, left, and right of the X-ray image 10 is equal to or greater than the second threshold has been shown in the aforementioned embodiment, the present invention is not limited to this. In the present invention, the non-irradiation region extractor 66 may be configured to use not only the above-described method based on calculating the difference between the pixel values of the adjacent pixels 21 (first derivative calculation) but also a boundary extraction method based on second derivative calculation in which the difference between the pixel values is further calculated.

While the processing of generating the DSA image 13 by the image processor 6 is described using a flowchart in a flow-driven manner in which the processing is performed in order along a processing flow for the convenience of illustration in the aforementioned embodiment, the present invention is not limited to this. In the present invention, the processing of generating the DSA image 13 by the image processor 6 may be performed in an event-driven manner in which the processing is performed on an event basis. In this case, the processing may be performed in a complete event-driven manner or in a combination of an event-driven manner and a flow-driven manner.

While the example in which the image processor 6 includes the image generator 61, the movement map generator 62, the smoothed movement map generator 63, the image movement processor 64, the composite image processor 65, the non-irradiated region extractor 66, the direct-ray region extractor 67, and the blood vessel image pixel extractor 68 has been shown in the aforementioned embodiment, the present invention is not limited to this. In the present invention, the structures of the image processor 6 other than the image generator 61, the movement map generator 62, the smoothed movement map generator 63, the image movement processor 64, and the composite image processor 65 can be omitted.

While the example of positional deviation correction using the movement vector 30 (and the smoothed movement vector 30a) performed when the DSA image 13 is generated based on the mask image 11, which is a non-contrast image, and the live image 12, which is a contrast image has been shown in the aforementioned embodiment, the present invention is not limited to this. The present invention is applicable to any positional deviation correction using the movement vector 30 (and the smoothed movement vector 30a) performed when two images obtained by imaging the same subject at different times are combined. For example, the present invention is applicable to generation of a long image, generation of an integrated image, or the like.

DESCRIPTION OF REFERENCE NUMERALS

2: imager
10: X-ray image (radiation image)
11: mask image (first image, non-contrast image)
11a: deformed image
12: live image (second image, contrast image)
13: DSA image (composite image)
20 (21, 22): pixel
21a: minimum pixel value difference pixel
30: movement vector (movement map)
30a: smoothed movement vector (smoothed movement map)
61: image generator
62: movement map generator
63: smoothed movement map generator
64: image movement processor
65: composite image processor
66: non-irradiation region extractor
67: direct-ray region extractor
68: blood vessel image pixel extractor
100: X-ray imaging apparatus (radiographic imaging apparatus)
B: blood vessel image
P: subject
T1: first threshold
T4: fourth threshold

The invention claimed is:

1. A radiographic imaging apparatus comprising:
an imager including an X-ray source and an X-ray tube device and configured to irradiate a subject with radiation and detect the radiation transmitted through the subject to image the subject;
an image generator constituted by a processor and configured to generate a first image and a second image obtained by imaging a same subject at different times;
a movement map generator constituted by the processor and configured to generate movement maps representing moving directions and movement amounts of a plurality of pixels which are at least a part of pixels belonging to the first image based on the first image and the second image;
a smoothed movement map generator constituted by the processor and configured to generate a smoothed movement map by suppressing high-frequency components of the movement maps in a spatial direction;
a pixel movement device constituted by the processor and configured to move a pixel of the first image based on the smoothed movement map and generate a deformed image;
a composite imager constituted by the processor and configured to generate a composite image in which the deformed image and the second image are combined; and
a blood vessel image pixel extractor constituted by the processor and configured to extract a pixel that constitutes a blood vessel image in a contrast image,
wherein the movement map generator is configured to generate the movement maps including movement vectors representing the moving directions and the movement amounts of each of the plurality of pixels which are at least the part of the pixels belonging to the first image based on the difference between the pixel value of one pixel of the second image and the pixel value of each of a plurality of pixels belonging to a region including a pixel of the first image corresponding to the one pixel,
wherein the smoothed movement map is generated by smoothing the movement vectors of the movement maps,
wherein the first image is a non-contrast image that is a radiation image obtained by imaging the subject in a state in which no contrast medium is administration to blood vessels of the subject,
wherein the second image is the contrast image that is a radiation image obtained by imaging the subject in a state in which the contrast medium is administration to the blood vessels of the subject, and
wherein the pixel movement device is configured to set a movement amount of a pixel of the non-contrast image corresponding to the pixel that constitutes the blood vessel image to 0.

2. The radiographic imaging apparatus according to claim 1, wherein the movement map generator is configured to generate a movement map representing a moving direction and a movement amount of the pixel of the first image based on the pixel value of the pixel of the second image and a pixel value of a minimum pixel value difference pixel, which is the pixel of the first image having a smallest pixel value difference with respect to the pixel of the second image.

3. The radiographic imaging apparatus according to claim 1, wherein the pixel movement device is configured to set a movement amount of the pixel of the first image to 0 when a pixel value difference between a pixel value of a pixel of the second image and a pixel value of the pixel of the first image corresponding to that pixel is equal to or less than a first threshold.

4. The radiographic imaging apparatus according to claim 1, further comprising:
a collimator configured to narrow down an irradiation region of the radiation to the subject; and
a non-irradiation region extractor configured to extract a non-irradiation region of the radiation generated by operation of the collimator in the first image,
wherein the pixel movement device is configured to set the movement amounts of the pixels of the first image in the non-irradiation region extracted by the non-irradiation region extractor to 0.

5. The radiographic imaging apparatus according to claim 4, wherein the non-irradiation region extractor is configured to determine a region of the first image outside boundary pixels as the non-irradiation region, defining pixels adjacent to an outside in a vicinity of top, bottom, left, and right edges of the first image, each of which has a pixel value equal to or greater than a predetermined second threshold, as the boundary pixels.

6. The radiographic imaging apparatus according to claim 1, further comprising:
a direct-ray region extractor configured to extract a direct-ray region in the first image,
wherein the pixel movement device is configured to set the movement amounts of the pixels in the direct-ray region of the first image extracted by the direct-ray region extractor to 0.

7. The radiographic imaging apparatus according to claim 6, wherein the direct-ray region extractor is configured to determine a region of the first image in which pixel values of the pixels that constitute the first image are equal to or greater than a predetermined third threshold as the direct-ray region.

8. The radiographic imaging apparatus according to claim 1, wherein the blood vessel image pixel extractor is configured to determine a pixel that constitutes the contrast image as the pixel that constitutes the blood vessel image when a pixel value difference between a pixel value of the pixel that constitutes the contrast image and a pixel value of the pixel of the non-contrast image corresponding to that pixel is equal to or greater than a predetermined fourth threshold.

9. The radiographic imaging apparatus according to claim 8, wherein the pixel movement device is configured to gradually increase the movement amount of the pixel of the non-contrast image as the pixel value difference between the pixel value of the pixel that constitutes the contrast image and the pixel value of the pixel of the non-contrast image corresponding to that pixel decreases when that pixel value difference is smaller than the predetermined fourth threshold.

10. The radiographic imaging apparatus according to claim 1, wherein the pixel movement device is configured not to set, to 0, a movement amount of a pixel having a pixel value equal to or less than a predetermined fifth threshold among pixels of the non-contrast image corresponding to pixels of the contrast image determined as pixels that constitute the blood vessel image by the blood vessel image pixel extractor.

11. A radiographic imaging apparatus comprising:
an imager including an X-ray source and an X-ray tube device and configured to irradiate a subject with radiation and detect the radiation transmitted through the subject to image the subject;
an image generator constituted by a processor and configured to generate a first image and a second image obtained by imaging a same subject at different times;
a movement map generator constituted by the processor and configured to generate movement maps representing moving directions and movement amounts of at least some of pixels belonging to the first image based on the first image and the second image;
a smoothed movement map generator constituted by the processor and configured to generate a smoothed movement map by suppressing high-frequency components of the movement maps in a spatial direction;
a pixel movement device constituted by the processor and configured to move a pixel of the first image based on the smoothed movement map and generate a deformed image;
a composite imager constituted by the processor and configured to generate a composite image in which the deformed image and the second image are combined; and
a blood vessel image pixel extractor configured to extract a pixel that constitutes a blood vessel image in a contrast image,
wherein the movement map generator is configured to generate the movement maps of the pixels of the first image based on the difference between a pixel value of one pixel of the second image and a pixel value of each of a plurality of pixels belonging to a region including a pixel of the first image corresponding to the one pixel,
wherein the first image is a non-contrast image that is a radiation image obtained by imaging the subject in a state in which no contrast medium is administered to blood vessels of the subject,
wherein the second image is the contrast image that is the radiation image obtained by imaging the subject in a state in which the contrast medium is administered to the blood vessels of the subject,
wherein the pixel movement device is configured to set a movement amount of a pixel of the non-contrast image corresponding to the pixel that constitutes the blood vessel image to 0,
wherein the blood vessel image pixel extractor is configured to determine a pixel that constitutes the contrast image as the pixel that constitutes the blood vessel image when a pixel value difference between a pixel value of the pixel that constitutes the contrast image and a pixel value of the pixel of the non-contrast image corresponding to that pixel is equal to or greater than a predetermined fourth threshold, and
wherein the pixel movement device is configured to gradually increase the movement amount of the pixel of the non-contrast image as the pixel value difference between the pixel value of the pixel that constitutes the contrast image and the pixel value of the pixel of the non-contrast image corresponding to that pixel decreases when that pixel value difference is smaller than the predetermined fourth threshold.

* * * * *